United States Patent [19]

Shimizu et al.

[11] Patent Number: 4,889,952

[45] Date of Patent: Dec. 26, 1989

[54] (PHENYLETHENYL) PHENYLPROPIONALDEHYDE AND METHOD FOR PRODUCING (BENZOLYPHENYL) PROPIONIC ACID USING THE SAME

[75] Inventors: Isoo Shimizu; Yasuo Matsumura, both of Yokohama; Yutaka Arai, Tokyo, all of Japan

[73] Assignee: Nippon Petrochemical Company, Ltd., Japan

[21] Appl. No.: 166,633

[22] Filed: Mar. 11, 1988

[30] Foreign Application Priority Data

Mar. 12, 1987 [JP] Japan .................... 62-57098

[51] Int. Cl.$^4$ ............................. C07C 59/76
[52] U.S. Cl. ................... 562/460; 560/052; 568/425
[58] Field of Search ............ 562/52; 568/425; 560/013

[56] References Cited

U.S. PATENT DOCUMENTS

| | | | |
|---|---|---|---|
| 4,028,404 | 6/1977 | Bays et al. | 562/460 |
| 4,035,376 | 7/1977 | Janssen | 562/460 |
| 4,097,522 | 6/1978 | Barocchi | 562/460 |

FOREIGN PATENT DOCUMENTS

| | | |
|---|---|---|
| 2913770 | 10/1979 | Fed. Rep. of Germany . |
| 2914006 | 10/1979 | Fed. Rep. of Germany . |
| 5002614 | 1/1980 | Japan . |
| 6097249 | 8/1981 | Japan . |
| 2238234 | 4/1986 | Japan . |

Primary Examiner—Paul J. Killos
Attorney, Agent, or Firm—Scully, Scott, Murphy & Presser

[57] ABSTRACT

A novel compound of α-(3-(1-phenylethenyl)phenyl)-propionaldehyde and a method for producing α-(3-benzoylphenyl)propionic acid which is prepared by oxidizing the former compound as an intermediate. The method is characterized in the easiness in operation, the low cost and the high purity of the product.

19 Claims, No Drawings

(PHENYLETHENYL) PHENYLPROPIONALDEHYDE AND METHOD FOR PRODUCING (BENZOLYPHENYL) PROPIONIC ACID USING THE SAME

BACKGROUND OF THE INVENTION (1) Field of the Invention

This invention relates to α-(3-(1-phenylethenyl)-phenyl)propionaldehyde which is represented by the following formula (I) and a method for producing α-(3-benzoylphenyl)propionic acid which is represented by the following formula (II) using the above new compound as an intermediate.

α-(3-(1-Phenylethenyl)phenyl)propionaldehyde is an intermediate used for economically preparing α-(3-benzoylphenyl)propionic acid (tradename: ketoprofen) which is represented by the following formula (II) and is used as a medicine for the relief of pain, fever and inflammation.

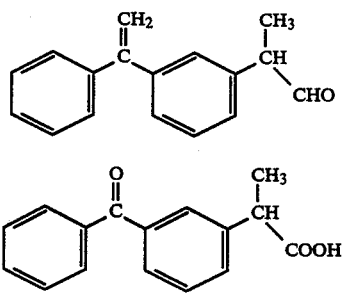

(2) Description of the Prior Art

With regard to the method for preparing ketoprofen, various methods have been proposed. Typical methods of them are exemplified as follows:

(1) Ketoprofen is prepared in a high yield by reacting 3-vinylbenzophenone with carbon monoxide in dilute hydrochloric acid in the presence of a palladium catalyst (U.S. Pat. No. 4,329,507).

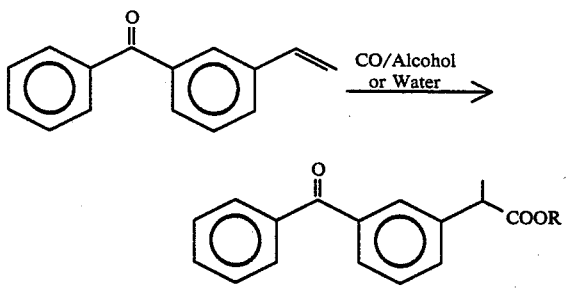

(2) 3-Acetylbenzophenone is reacted with chloroform in a basic condition of tertiary ammonium salt to obtain α-arylpropenoic acid and it is then subjected to catalytic hydrogenation reduction in the presence of palladium-carbon catalyst to obtain ketoprofen (Japanese Laid-Open Patent Publication No. 55-7225).

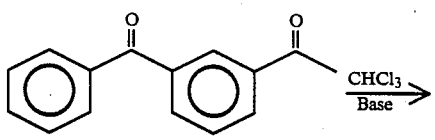

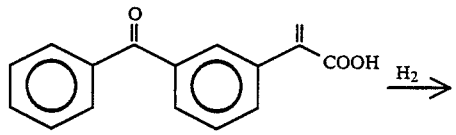

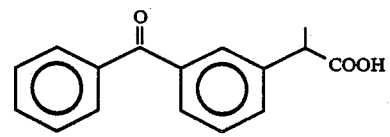

In both the above methods (1) and (2), the numbers of reaction steps are small and the aimed product can be obtained in high yields. However, because it cannot be said that the synthesis of starting materials is easy, the above methods are not satisfactory in view of industrial production.

BRIEF SUMMARY OF THE INVENTION

It is, therefore, the primary object of the present invention to provide a new intermediate which is useful for synthesizing ketoprofen without difficulty in a high yield and at a low cost using easily available raw materials.

Another object of the present invention is to provide a novel method for producing the α-(3-benzoylphenyl)-propionic acid using this new intermediate compound.

That is, the new method of the present invention to produce α-(3-benzoylphenyl)propionic acid represented by the formula (II) is characterized in that the new compound of α-(3-(1-phenylethenyl)phenyl)propionaldehyde of the formula (I) is oxidized in one step or in sequential steps. The compounds represented by the following formulae include their optical isomers.

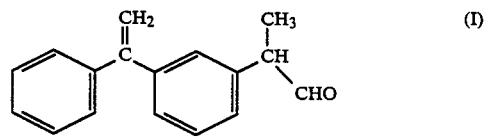

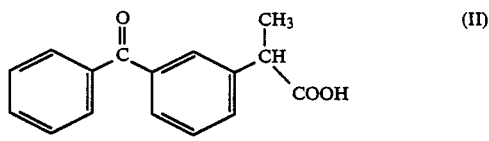

DETAILED DESCRIPTION OF THE INVENTION

The α-(3-(1-phenylethenyl)phenyl)propionaldehyde of the formula (I) can be synthesized without difficulty, for example, by the following procedure.

A method to use acetophenone as a starting material will be described. Acetophenone is reacted with a Grignard reagent of m-vinylphenylmagnesium bromide to obtain 1,1-(3-vinylphenyl)phenylethyl alcohol (hereinafter referred to as "VPA"). The reaction product is then dehydrated in the presence of potassium hydrogensulfate to form 1-(3-vinylphenyl)-1-phenylethylene (formula III). This Grignard addition reaction is carried out at a temperature in the range of 0° to 100° C., preferably 20° to 80° C. The dehydration is carried out at 170° to 250° C., preferably 190° to 230° C., at a reduced pressure. The quantity of Grignard reagent is 1.0 to 1.2 equivalents relative to the acetophenone.

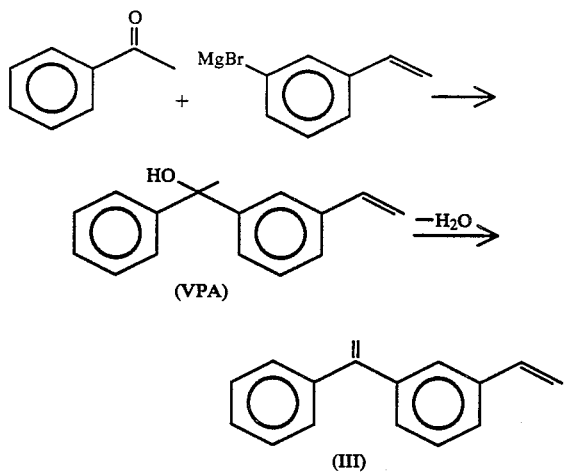

The α-(3-(1-phenylethenyl)phenyl)propionaldehyde can be prepared by the hydroformylation of the obtained 1-(3-vinylphenyl)-1-phenylethylene in an ordinary manner.

That is, 1-(3-vinylphenyl)-1-phenylethylene represented by the formula (III) is reacted with hydrogen and carbon monoxide at a temperature of 40° to 150° C. in the presence of a transition metal carbonylation catalyst to obtain α-(3-(1-phenylethenyl)phenyl)propionaldehyde of the formula (I).

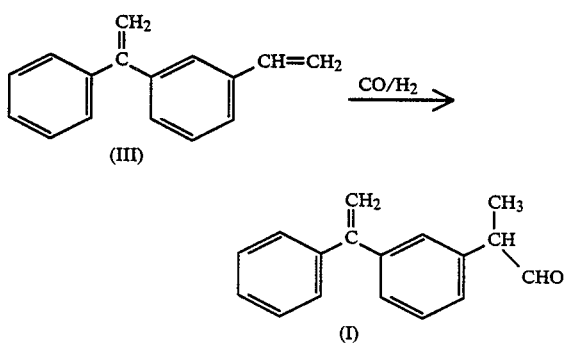

The above α-(3-(1-phenylethenyl)phenyl)propionaldehyde of the formula (I) is a new compound. This compound can be prepared more easily and economically by the following process.

When benzene is alkylated with ethylene in the presence of an alkylation catalyst to obtain ethylbenzene, 1-(3-ethylphenyl)-1-phenylethane (formula IV) is also simultaneously produced. This 1-(3-ethylphenyl)-1-phenylethane is then dehydrogenated in the presence of a dehydrogenation catalyst to obtain 1-(3-vinylphenyl)-1-phenylethylene (formula III). By the hydroformylation of it in an ordinary method, the foregoing α(3-(1-phenylethenyl)phenyl)propionaldehyde can be prepared.

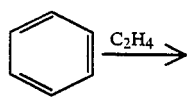

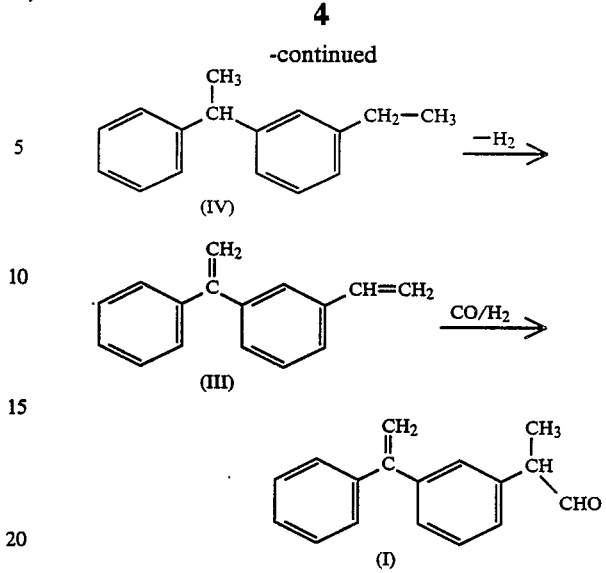

The above will be described in more detail.

When benzene is alkylated with ethylene in the presence of an alkylation catalyst, a reaction product containing unreacted benzene, alkylbenzenes, polyalkylbenzenes and heavier products is obtained. The above 1-(3-ethylphenyl)-1-phenylethane of the formula (IV) is recovered as a fraction mainly containing components having boiling points of 285° to 290° C. (as atmospheric pressure) by distillation such as reduced-pressure distillation. The fraction is then dehydrogenated in the presence of a dehydrogenation catalyst, and if necessary, it is followed by distillation, to obtain 1-(3-vinylphenyl)-1-phenylethylene.

Exemplified as the catalysts for the alkylation of benzene are Lewis acids such as metal halides, for example, aluminum chloride, iron chloride and boron trifluoride; protonic acids such as hydrogen fluoride and phosphoric acid; and solid acids such as silica-alumina and crystalline alumino-silicate of ZSM-5 type synthetic zeolite. In addition, solid catalysts such as the one in which a protonic acid like phosphoric acid is carried on a carrier of diatomaceous earth, can be exemplified. Especially preferable catalysts are metal halides such as aluminum chloride and ZSM-5 type synthetic zeolite catalysts, known as ZSM-5 and ZSM-11.

These ZSM-5 type synthetic zeolites are described in detail in the following patent gazettes.

ZSM-5:U.S. Pat. No. 3,702,886; and British Patent No. 1,161,974

ZSM-11:U.S. Pat. No. 3,709,979

In general, the molar ratio as $SiO_2/Al_2O_3$ of the ZSM-5 type catalysts are 20 to 400 and the catalysts exhibit specific X-ray diffraction patterns. Detailed characteristic description is given in the above patent gazettes.

The synthetic zeolites used in the present invention are those which are ion-exchanged with hydrogen ion or divalent ions such as calcium, magnesium, strontium and barium ions, or trivalent ions such as rare earth elements of cerium and yttrium. Besides them, the synthetic zeolites which are modified with boron, gallium, phosphorus or their compounds can also be used.

The alkylation of benzene with ethylene can be carried out both in a vapor phase and a liquid phase. For example, the temperature as a condition for alkylation in vapor phase is in the range of 300° to 650° C., preferably 350° to 550° C. The pressure for the alkylation is not especially restricted, however, it is generally done at 1 to 100 kg/cm² and preferably at atmospheric pressure. The preferable molar ratio of materials to be fed to the reaction system as "ethylene/benzene" is 0.05 to 5. The WHSV is in the range of 1 to 500 and preferably 1 to 300.

In the reaction in liquid phase, the reaction temperature is about 20° to 175° C. and preferably about 90° to 150° C. The reaction pressure may be a value at which the reaction system can be maintained in a liquid phase, for example, about 0.5 to 14 kg/cm². The duration of reaction is generally in the range of about 10 minutes to 10 hours, and preferably about 20 minutes to 3 hours.

By alkylating benzene with ethylene, a reaction mixture comprising unreacted benzene, ethylbenzenes, polyethylbenzenes and heavier products, is obtained. In this heavier products, the 1-(3-ethylphenyl)phenylethane and also tarry substance are contained.

The heavier products may be once recovered from the above reaction products by distillation. A fraction containing 1-(3-ethylphenyl)-1-phenylethane is recovered by distillation such as reduced pressure distillation directly from the above reaction mixture or through the above heavier products. The fraction containing 1-(3-ethylphenyl)-1-phenylethane is obtained as a fraction mainly containing components having a boiling point of 285° to 290° C. (as atmospheric pressure).

As the above-described alkylation reaction can be exemplified by the process for preparing ethylbenzene which is widely adopted for the industrial preparation of styrene by dehydrogenation of the ethylbenzene. For example, in industrial methods, an aluminum chloride process using aluminum chloride catalyst, a high-pressure process using alumina catalyst carried on silica gel that was developed by Koppers Gmbh, a solid phosphoric acid process using a solid catalyst in which phosphoric acid is impregnated in diatomaceous earth that was developed by Universal Oil Products Co., an alkar process using a catalyst of boron fluoride or its complex also developed by the above U.O.P. CO., and a zeolite process using a zeolite catalyst that was developed by Mobil Oil Corp.

Dehydrogenation Reaction

In the present invention, the fraction containing the above 1-(3-ethylphenyl)-1-phenylethane is subjected to dehydrogenation in the presence of a dehydrogenation catalyst. As the dehydrogenation catalyst for this purpose, the conventional catalysts that are used in the dehydrogenation of ethylbenzene to prepare styrene can be used. For example, catalysts containing iron, chromium or mixture thereof such as chromia-alumina catalyst and iron oxide catalyst can be used. These catalysts can be used together with a promoter such as potassium carbonate or the oxide of chromium, cerium, molybdenum or vanadium.

In view of the chemical equilibrium, with regard to the pressure as a reaction condition for dehydrogenation, the reaction can proceed in a lower pressure, and the higher the temperature is, the further the reaction proceeds because it is an endothermic reaction. Accordingly, the reaction temperature is generally selected from the range of 500° to 700° C., and preferably 550° to 650° C. At a temperature below 500° C., the dehydrogenation reaction cannot substantially proceed. On the other hand, temperatures above 700° C. is not desirable because side reactions such as decomposition is caused to occur. The reaction pressure is from a reduced pressure to 5 kg/cm², and preferably from a reduced pressure to 3 kg/cm². In general, excess steam is used as a heating medium.

The contact time length in a continuous flow system is selected from the range of 0.01 to 10 hr$^{-1}$ as LHSV.

After the reaction, 1-(3-vinylphenyl)-1-phenylethylene is obtained by distillation, preferably by reduced pressure distillation.

Because the 1-(3-vinylphenyl)-1-phenylethylene obtained by the dehydrogenation has a higher boiling point as compared with that of the corresponding saturated compounds in the starting materials, the separation by distillation can be done more easily.

The thus obtained 1-(3-vinylphenyl)-1-phenylethylene is then subjected to hydroformylation in a conventional manner to prepare α-(3-(1-phenylethenyl)-phenyl)propionaldehyde.

Hydroformylation

In this step, 1-(3-vinylphenyl)-1-phenylethylene is reacted with hydrogen and carbon monoxide at a temperature of 40° to 150° C. in the presence of a transition metal carbonylation catalyst to prepare α-(3-(1-phenylethenyl)phenyl)propionaldehyde of the formula (I).

The complex catalysts used in this step are complexes of transition metals such as Ni, Co, Fe, Mo, Pt, Rh, Ir, Ru and Re. Among them, the complexes of precious metals such as Pt, Rh, Ir, Ru and Re are preferable. As the transition metals, those having oxidation numbers from 0 to the highest numbers can be used. Usable complexes are those having ligands of halogen atoms, trivalent phosphorus compounds, π-allyl group, amines, nitriles, oximes, olefins, hydrogen, or carbon monoxide.

The transition metal complex catalysts are exemplified by bistriphenylphosphine dichlorocomplex, bistributylphosphine dichlorocomplex, bistricyclohexylphosphine dichlorocomplex, π-allyltriphenylphosphine dichlorocomplex, triphenylphosphine piperidine dichlorocomplex, bisbenzonitrile dichlorocomplex, biscyclohexyloxime dichlorocomplex, 1,5,9-cyclododecatriene dichlorocomplex, bistriphenylphosphine dicarbonyl complex, bistriphenylphosphine acetate complex, bistriphenylphosphine dinitrate complex, bistriphenylphosphine sulfate complex, tetrakistriphenylphosphine complex; and complexes in which a part of ligands are carbon monoxide such as chlorocarbonyl bistriphenylphosphine complex, hydridocarbonyl tristriphenylphosphine complex, bischlorotetracarbonyl complex and dicarbonyl acetylacetonate complex.

Furthermore, the compounds which produce the above metal complexes in the reaction system can be also used. That is, phosphine, nitrile, allyl compound, amine, oxime, olefin or carbon monoxide which is able to be the ligands to the oxides, sulfates or chlorides of the above transition metals, are simultaneously added into the reaction system.

The above phosphines are exemplified by triphenylphosphine, tritolylphosphine, tributylphosphine, tircyclohexylphosphine and triethylphosphine. The nitriles are exemplified by benzonitrile, acrylonitrile, propionitrile and benzylnitrile. The allyl compounds are exemplified by allyl chloride and allyl alcohol. The amines are exemplified by benzylamine, pyridine, piperazine and tri-n-butylamine. The oximes are exemplified by cyclohexyloxime, acetoxime and benzaldoxime. The olefins are exemplified by 1,5-cyclooctadiene and 1,5,9-cyclododecatriene.

The use quantity of a complex catalyst or a compound which can produce a complex is 0.0001 to 0.5 mole, preferably 0.001 to 0.1 mole to one mole of 1-(3-vinylphenyl)1-phenylethylene (formula III). When the compound which produces a complex is used, the addition quantity of the compound to form ligands is 0.8 to 10 moles, preferably 1 to 4 moles, to one mole of the compound to produce a complex.

Furthermore, for the purpose of improving the rate of reaction, it is possible to add inorganic halides such as hydrogen chloride and boron trifluoride, or organic iodide such as methyl iodide.

When these halides are added, the quantities of them are 0.1 to 30 moles, preferably 1 to 15 moles, as halogen atoms to 1 mole of the complex catalyst or the compound to produce a complex. Even though it depends upon the kind of catalyst, if the addition quantity is less than 0.1 mole, the effect of the addition cannot be observed sometimes. If the addition quantity exceeds 30 times by moles, not only the catalytic activity is lowered but also halogen atoms are added to the double bonds of 1-(3-vinylphenyl)-1-phenylethylene which fact is a bar to the aimed reaction.

The hydroformylation is carried out at a temperature in the range of 40° to 150° C., preferably 55° to 110° C. If the reaction temperature is below 40° C., the rate of reaction is very low which is not acceptable in industrial production processes. On the other hand, if the reaction temperature is above 150° C., it is not desirable because side reactions of polymerization and addition of hydrogen and decomposition of complex catalyst are caused to occur.

If the reaction pressure is 5 kg/cm² or above, it can be selected arbitrarily. When the reaction pressure is lower than 5 kg/cm², the rate of reaction is very low, which cannot be adopted practically. When the reaction pressure is higher, the reaction proceeds faster. However, a too high pressure necessitates a very high pressure resistance for a reaction vessel, so that there is naturally a limit in view of the designing of reaction equipment. Accordingly, it is sufficient that the pressure is not higher than 500 kg/cm² in a practical view point.

The reaction is continued until the lowering of pressure owing to the absorption of the mixed gas of carbon monoxide and hydrogen, is not observed. The reaction time of 4 to 20 hours is generally sufficient.

The carbon monoxide and hydrogen that are necessary for the reaction can be fed either separately or by mixing them previously. The molar ratio of carbon monoxide and hydrogen to be fed into the reaction system can be selected arbitrary. In this hydroformylation, carbon monoxide and hydrogen are consumed or absorbed accurately at a molar ratio of 1:1. Accordingly, because a component which is supplied in excess remains unreacted, the reaction can be proceeded again if the other component is supplied at the time when the lowering of pressure decrease is observed. Even though it will depend upon the size of reaction vessel and the mode of reaction, it is generally most effective that carbon monoxide and hydrogen are fed in a molar ratio of 1:1.

In the above hydroformylation, it is possible to use a solvent which is inert to the reaction in order to remove the heat of reaction or the like. Exemplified as the solvents that are inert to the hydroformylation are polar solvents such as ethers, ketones and alcohols, and nonpolar solvents such as paraffins, cycloparaffins and aromatic hydrocarbons. However, satisfactory result can be obtained generally even when any solvent is not used.

After the hydroformylation, the reaction product is subjected to separation, preferably by distillation under a reduced pressure and the aimed product of α-(3-(1-phenylethenyl)phenyl)propionaldehyde (formula I) and catalyst can be separated quite easily. The recovered complex catalyst can be used again for the next hydroformylation process. The thus obtained hydroformylation product of α-(3-(1-phenylethenyl)phenyl)propionaldehyde (formula I) is then oxidized in one step or in sequential steps using an oxidizing agent to obtain α-(3-benzoylphenyl)propionic acid (formula II), that is, ketoprofen.

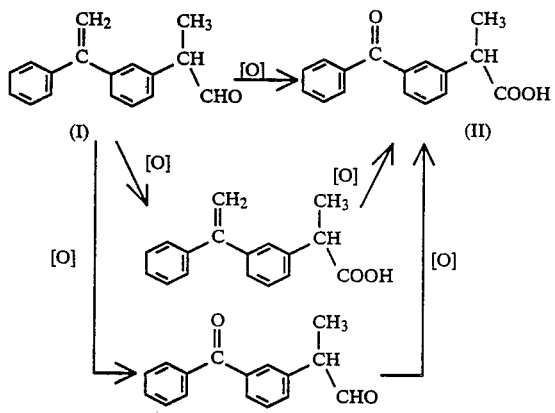

Oxidation

This oxidation will be described in detail.

In the oxidation, the vinylidene group and the formyl group of α-(3-(1-phenylethenyl)phenyl)propionaldehyde (formula I) are oxidized. It is possible to oxidize both the vinylidene group and formyl group simultaneously in one step reaction. Meanwhile, it is also possible to combine two steps in which the vinylidene group is firstly oxidized and the formyl group is then oxidized. Furthermore, the order of oxidation can be reversed.

When the vinylidene group is firstly oxidized, α-(3-benzoylphenyl)propionaldehyde is formed as a partially oxidized product. In this case, it is possible to block the formyl group, for example, as an acetal group by a known method using a suitable blocking agent. When the formyl group is firstly oxidized, α-(3-(1-phenylethenyl)propionic acid is also obtained as a partially oxidized product. These compounds are further oxidized to obtain α(3-benzoylphenyl)propionic acid of ketoprofen, the aimed product in the present invention.

The above oxidation can be done according to a known oxidation method. For example, there are an oxidation method with molecular oxygen in the presence of an oxidation catalyst and other oxidation method using an oxidizing agent such as permanganate, manganese dioxide, chromate, lead tetraacetate, periodate, ruthenium tetraoxide, osmium tetraoxide, hydrogen peroxide, selenium dioxide, ozone, and a mixture of them.

By carrying out one-step oxidation by any one of these oxidation methods, that is, the simultaneous oxidation; or by carrying out two-step oxidation by combining any of two oxidation methods, that is, the sequential oxidation; it is possible to prepare α-(3-benzoylphenyl)-propionic acid (formula II) from α-(3-(1-phenylethenyl)phenyl)propionaldehyde (formula I).

The catalyst used in the oxidation with molecular oxygen are exemplified by the salts of metals selected from the groups VI-B, VII-B and VIII of the periodic table such as chromium, manganese, tungsten, molybdenum, platinum, palladium, cobalt, nickel, iron, rhodium, and ruthenium, or their mixtures. Among them, the salts of cobalt, iron, manganese, and chromium are preferable. The suitable quantity of a catalyst to be used is 0.05 to 10% by weight to the quantity of raw material. As the molecular oxygen, pure oxygen or the air can be used. Furthermore, it is possible to supply the reaction system with a mixture of pure oxygen and other inert gases.

The reaction temperature in the oxidation using molecular oxygen is 30° to 250° C., and preferably 50° to 200° C. In the case that the reaction temperature is lower than 30° C., the rate of reaction is very low, and in the case that the reaction temperature exceeds 250° C., the selectivity to the aimed product is seriously lowered, both of which are not desirable.

In order to improve the efficiency in the contact of starting materials with an oxidizing agent, a solvent can be used. Such a solvent is exemplified by water, acetone, alcohols such as tert-butyl alcohol, glacial acetic acid, acetic acid, isooctane, benzene, chloroform, and pyridine. They are used singly or as a mixture of them.

The quantity of oxidizing agent such as a permanganate to be added is at least 1 equivalent, preferably more than 1.5 equivalent, to the raw material. There is not especially the upper limit of the use quantity, however, the quantity of more than 10 equivalent is not desirable because it is only uneconomical. The temperature of oxidation using the oxidizing agent is 0° to 200° C. and preferably 30° to 150° C. The reaction cannot proceed at temperatures below 0° C., while by-products are formed and the selectivity to the aimed product is seriously lowered at temperatures above 200° C., both of which are not desirable.

It is, in either case, a remarkable feature of the compound of formula (I) that its ethylidene groups and formyl groups are easily oxidized respectively.

After the oxidation, the oxidizing agent or oxidation catalyst is separated, for example, by filtration, or the reaction mixture is extracted with an organic solvent such as benzene, ethyl acetate, or chloroform. After that, highly pure α-(3-benzoylphenyl)propionic acid, ketoprofen, is obtained by the conventional distillation, recrystallization or the combination thereof.

As described above, it is possible to prepare easily ketoprofen at low cost and in a high yield by way of the novel intermediate, α-(3-(1-phenylethenyl)phenyl)propionaldehyde that is proposed in the present invention. Because substituent groups of the compound according to the present invention are specified, ketoprofen having particular effect to relief inflammation can be produced by using the compound.

The present invention will be described with reference to examples which by no means limit the present invention.

EXAMPLE 1

Synthesis of 1-(3-vinylphenyl)-1-phenylethylene (formula III)-(1)

To a 2 liter three-neck flask equipped with a dropping funnel, a reflux condenser, and a stirrer was added 25.5 g (1.05 mole) of metallic magnesium and it was dried sufficiently by supplying dry nitrogen gas. After that, 50 ml of tetrahydrofuran which had been dried with a molecular sieve 5A, was put into the flask and the contents were stirred vigorously. A solution of 183 g (1.0 mole) of 3-vinylbenzene bromide in 500 ml of dried tetrahydrofuran was dropped little by little for 2 hours. The reaction temperature was maintained 75 to 80° C. and, after the addition of the solution, the stirring was continued for further 1 hour as it stands. Into the thus obtained Grignard reagent of 3-vinylphenylmagnesium bromide, a solution of 122.6 g (1.02 mole) of acetophenone in 500 ml of dried tetrahydrofuran was dropped little by little for 2 hours. The reaction temperature was maintained at 75° to 80° C. and, after the dropping, the stirring was continued for further 1 hour as it stands. The reaction mixture was then poured into 3 liter of an aqueous solution of 75 g of ammonium chloride and it was left to stand still for 20 hours and an oily layer was recovered to obtain 1,1-(3-vinylphenyl)phenylethyl alcohol (VPA) in a yield of 89% (acetophenone basis) by distilling off the tetrahydrofuran.

To a 300 ml three-neck flask with a distillation column and a dropping funnel was added 81 g of potassium hydrogensulfate and the pressure was reduced to 15 to 20 mmHg. The obtained alcohol was then dropped into the flask little by little for 2 hours. The water and oily components produced by dehydration were recovered from the top of the distillation column and 1-(3-vinylphenyl)-1-phenylethylene was obtained in a yield of 100% (VPA basis) from the oily layer by a separatory funnel. The dehydration reaction was carried out at a temperature of 200° to 250° C.

The analytical data on the thus produced 1-(3-vinylphenyl)-1-phenylethylene (formula III) are shown in the following:

Boiling Point: 134.0°–135.5° C./2–3 mmHg

IR: (Neat) cm$^{-1}$: 3050, 1690, 1495, 1260, 995, 900, 810, 780, 700

$^1$H—NMR: (CCl$_4$, δppm): 7.10–7.70 (9H Multiplet) 6.65–6.80 (1H Quadruplet) 5.65–5.80 (1H Doublet) 5.45–5.50 (2H Doublet) 5.20–5.30 (1H Doublet)

Elemental Analysis: (as C$_{16}$H$_{14}$): Calculated: C: 93.20%, H: 6.80%, Found: C: 93.24%, H: 6.76%.

EXAMPLE 2

Preparation of
α-(3-(1-phenylethenyl)phenyl)propionaldehyde-(1)

To a 500 ml autoclave with a stirrer were added 50 g of 1-(3-vinylphenyl)-1-phenylethylene and 0.6 g of rhodium hydridocarbonyl tristriphenylphosphine. The pressure was raised up to 60 kg/cm$^2$ by a mixed gas of hydrogen and carbon monoxide (1:1 in molar ratio) and reaction was continued until the absorption of the mixed gases caused by the reaction was not observed. The reaction temperature was 60° C. After the reaction, the temperature was lowered to room temperature and unreacted mixed gases were removed to recover the reaction product. This was subjected to reduced pressure distillation to obtain α-(3-(1-phenylethenyl)phenyl)propionaldehyde in a yield of 73% (on the basis of 1-(3-vinylphenyl)-1-phenylethylene) at a distilling temperature of 125.5°–126.5° C./0.5–1 mmHg. As a result of GC analysis, it was understood that the α-(3-(1-phenylethenyl)phenyl)propionaldehyde was 96%. The results of spectrum analysis are shown in the following.

IR: (Neat) cm$^{-1}$: 3055, 2995, 2850, 2730, 1740, 1620, 1500, 1445, 1380, 1060, 900, 750, 700

$^1$H-NMR: (CCl$_4$, δppm): 9.80 (1H Singlet) 6.90–7.45 (9H Multiplet) 3.05–3.55 (1H Quadruplet) 5.09 (2H Singlet) 1.30–1.47 (3H Doublet)

Elemental Analysis: (as C$_{17}$H$_{16}$O): Calculated: C: 86.44%, H: 6.78%, O: 6.78%, Found: C: 86.50%, H: 6.80%, O: 6.70%.

EXAMPLE 3

Synthesis of 1-(3-vinylphenyl)-1-phenylethylene-(2)

-Alkylation-

From the reaction mixture in ethylbenzene preparation process for producing polystyrene by reacting benzene with ethylene using aluminum chloride catalyst, a fraction having a boiling point of 285°–290° C. (at atmospheric pressure) was recovered by distilling off the unreacted benzene, ethylbenzene and polyethylbenzene through reduced pressure distillation. In this fraction, 85% by weight of 1-(3-ethylphenyl)-1-phenylethane was contained. Besides this compound, other components such as tetralin, indane, naphthalene, fluorene, alkyl derivatives of them and substances, the structures of which were unknown, were also contained in this fraction.

-Dehydrogenation-

A dehydrogenation catalyst (trademark: 64C made by Nissan Girdler Catalysts Co., Ltd.) of 0.5–1 mm in particle diameter was fed into a fixed bed continuous flow reactor made of a stainless steel tube of 10 mm in inner diameter and 60 cm in length, thereby forming a catalyst bed of 20 cm in height. An oily substance containing 82% of 1-(3-ethylphenyl)-1-phenylethane and pure water in a ratio of 1:5 were preheated respectively to be vaporized, and they were mixed together and fed to the catalyst bed at a temperature of 550° C. and an SV of 0.25. Reaction product was cooled to room temperature and the vapor phase and liquid phase were separated to obtain an organic layer, which was subjected to reduced-pressure distillation at 2–3 mmHg to obtain a fraction of 133°–137° C. As a result of GC analysis, it was understood that the fraction contained 86% by weight of 1-(3-vinylpenyl)-1-phenylethylene and 14% by weight of other hydrocarbons.

EXAMPLE 4

Preparation of α(3-(1-phenylethenyl)phenyl)propionaldehyde-(2)

To a 500 ml autoclave with a stirrer were added 50 g of the fraction obtained in Example 3 mainly containing 1-(3-vinylphenyl)-1-phenylethylene and 0.6 g of rhodium hydridocarbonyl tristriphenylphosphine. The pressure was raised up to 60 kg/cm$^2$ by a mixed gas of hydrogen and carbon monoxide (1:1 in molar ratio) and reaction was continued until the absorption of the mixed gases caused by the reaction was not observed. The reaction was carried out at 60° C. After the reaction, the temperature was lowered to room temperature and unreacted mixed gases were removed to recover a reaction product. This reaction product was subjected to reduced pressure distillation to obtain α-(3-(1-phenylethenyl)phenyl)propionaldehyde in a yield of 73% (on the basis of 1-(3-vinylphenyl)-1-phenylethylene) at a distilling temperature of 125.5°–126.5° C./0.5–1 mmHg. As a result of GC analysis, it was understood that the α-(3-(1-phenylethenyl)phenyl)propionaldehyde was 96%.

EXAMPLE 5

Preparation of α-(3-benzoylphenyl)propionic acid (ketoprofen)-(1)

To a 300 ml reaction vessel with a stirrer were fed 15 g of α(3-(1-phenylethenyl)phenyl)propionaldehyde obtained in Example 2, 0.03 g of cobalt naphthenate and 100 ml of acetic acid as a solvent, and 150 ml/min of pure oxygen was fed into the vessel for 16 hours at a reaction temperature of 120° C. After the reaction, the solvent was removed by reduced-pressure distillation to obtain a solid substance. The solid substance was washed five times with 500 ml of water and it was dissolved in 500 ml of ether and washed three times again with water. After that, the ether was removed by reduced-pressure distillation and the product was finally recrystallized with a benzene/petroleum ether mixture to obtain 10 g of α(3-benzoylphenyl)propionic acid (ketoprofen). The properties such as the melting point and the spectrum of the final product were the same as those of an authentic sample.

EXAMPLE 6

Preparation of α-(3-benzoylphenyl)propionic acid (ketoprofen)-(2)

Reaction was carried out in the like manner as Example 5 except that 200 ml/min of air dried with silica gel was used in place of the pure oxygen and the temperature of the reaction was 150° C., thereby obtaining 8.6 g of ketoprofen. The properties such as the melting point and the spectrum of the product were the same as those of an authentic sample.

Furthermore, α-(3-(1-phenylethenyl)phenyl)propionic acid and α(3-benzoylphenyl)propionaldehyde were confirmed as partial oxidized products of α-(3-(1-phenylethenyl)phenyl)propionaldehyde in the reaction mixture.

EXAMPLE 7

Preparation of α-(3-benzoylphenyl)propionic acid (ketoprofen)-(3)

α-(3-(1-Phenylethenyl)phenyl)propionaldehyde (36 g) obtained in Example 4 was dissolved in 250 ml of benzene and 250 ml of water was further added thereto with vigorous stirring to prepare a suspension. Then, 2 liter of 2% aqueous solution of potassium permanganate was dropped little by little over 1.5 hours. After the dropping, stirring was continued for 18 hours at room temperature. After the reaction, it was acidified by adding concentrated sulfuric acid and was treated by adding 35 g of sodium sulfite. After that, 500 ml of water was added and extraction was carried out three times with 150 ml of ether. The ether solution was washed with water and it was extracted with 5% aqueous solution of sodium hydroxide. The aqueous layer was acidified by adding hydrochloric acid and extracted again with ether, which was followed by washing with water, drying with anhydrous magnesium sulfate, and filtration. The ether was then removed by reduced-pressure evaporation. Finally, 20 g of α(3-benzoylphenyl)propionic acid (ketoprofen) was obtained by re-crystallization from benzene/petroleum ether mixture. The melting point and spectrum were the same as those of an authentic sample.

What is claimed is:

1. α-(3-(1-Phenylethenyl)phenyl)propionaldehyde which is represented by the following formula (I):

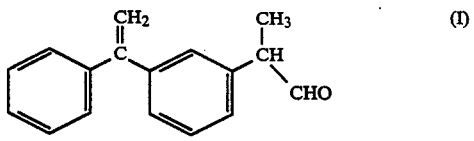

2. A method for producing α-(3-benzoylphenyl)propionic acid represented by the following formula (II) which comprises reacting α-(3-(1-phenylethenyl)phenyl) propionaldehyde with an oxidizing effective amount of molecular oxygen in the presence of a catalytic effective amount of an oxidation catalyst or an oxidizing effective amount of an oxidizing agent under oxidation conditions.

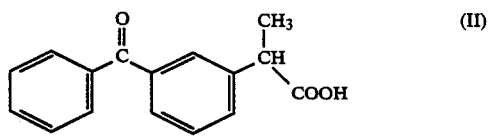

3. The method in claim 2, wherein said α-(3-(1-phenylethenyl)phenyl)propionaldehyde is prepared by reacting a fraction containing 1-(3-vinylphenyl)-1-phenylethylene with hydrogen and carbon monoxide in the presence of a transition metal complex catalyst.

4. The method in claim 3, wherein said fraction containing 1-(3-vinylphenyl)-1-phenylethylene is prepared by dehydrogenating a fraction containing 1-(3-ethylphenyl)-1phenylethane.

5. The method in claim 4, wherein the fraction containing said 1-(3-ethylphenyl)-1-phenylethane is the one which is recovered as a fraction mainly containing compounds having a boiling point of 285°–290° C. (at atmospheric pressure) from the process of alkylating benzene with ethylene in the presence of an alkylation catalyst.

6. The method in claim 5, wherein said alkylation catalyst is a Lewis acid or a protonic acid.

7. The method in claim 6, wherein said Lewis acid is aluminum chloride.

8. The method in claim 1, wherein said oxidation is carried out by way of the oxidation of α-(3-(1-phenylethenyl)phenyl)propionic acid and/or α-(3-benzoylphenyl)propionaldehyde.

9. The method according to claim 2 wherein the oxidation catalyst is a transition metal salt wherein said transition metal is a Group VI B, VII B or VIII metal.

10. The method according to claim 9 wherein the transition metal is chromium, manganese, tungsten, molybdenum, platinum, palladium, cobalt, nickel, iron, rhodium, or ruthenium or mixtures thereof.

11. The method according to claim 10 wherein the metal is iron or chromium or mixtures thereof.

12. The method according to claim 2 wherein the oxidizing agent is permangenate, manganese dioxide, chromate, lead tetracetate, periodate, ruthenium tetraoxide, osmium tetraoxide, hydrogen peroxide, selenium dioxide, ozone or a mixture thereof.

13. The method of claim 3 wherein the transition metal is nickel, cobalt, iron, molybdenum, platinum, rhodium, ruthenium or rhenium.

14. The method of claim 4 wherein the 1-(3-ethylphenyl)1-phenylethane is dehydrogenated in the presence of an effective amount of a dehydrogenation catalyst.

15. The method of claim 14 wherein the dehydrogenation catalyst contains iron, chromium or a mixture thereof.

16. The method of claim 15 wherein a dehydrogenation catalyst promoter is additionally present.

17. The method of claim 16 wherein the promoter is potassium carbonate or the oxide of cerium, molybdenum or vanadium.

18. The method of claim 12 wherein the temperature ranges from 0° to 200° C.

19. The method of claim 9 wherein the temperature ranges from 30° to 250° C.

* * * * *